(12) United States Patent
McKay

(10) Patent No.: US 8,673,019 B2
(45) Date of Patent: Mar. 18, 2014

(54) USE OF ANTI-INFLAMMATORY COMPOUNDS WITH ALLOGRAFT TISSUE IMPLANTATION

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1463 days.

(21) Appl. No.: 11/403,589

(22) Filed: Apr. 13, 2006

(65) Prior Publication Data

US 2007/0240725 A1 Oct. 18, 2007

(51) Int. Cl.
*A61F 2/28* (2006.01)

(52) U.S. Cl.
USPC ........................................... 623/23.63

(58) Field of Classification Search
USPC ............................................ 623/23.63, 908
See application file for complete search history.

(56) References Cited

U.S. PATENT DOCUMENTS

| | | | |
|---|---|---|---|
| 4,846,835 A * | 7/1989 | Grande | 128/898 |
| 4,913,903 A | 4/1990 | Sudmann et al. | |
| 5,324,519 A | 6/1994 | Dunn et al. | |
| 5,707,647 A | 1/1998 | Dunn et al. | |
| 5,916,585 A | 6/1999 | Cook et al. | |
| 6,033,582 A * | 3/2000 | Lee et al. | 216/37 |
| 6,190,412 B1 * | 2/2001 | Lee et al. | 623/16.11 |
| 6,200,347 B1 | 3/2001 | Anderson et al. | |
| 6,294,187 B1 * | 9/2001 | Boyce et al. | 424/422 |
| 6,602,296 B1 | 8/2003 | Day et al. | |
| 2003/0045942 A1 * | 3/2003 | Lai et al. | 623/23.51 |
| 2003/0109686 A1 | 6/2003 | Sampath et al. | |
| 2004/0002770 A1 * | 1/2004 | King et al. | 623/23.51 |
| 2005/0008620 A1 * | 1/2005 | Shimp et al. | 424/93.7 |
| 2005/0208095 A1 * | 9/2005 | Hunter et al. | 424/423 |
| 2005/0261767 A1 | 11/2005 | Anderson et al. | |
| 2007/0173950 A1 * | 7/2007 | Zanella et al. | 623/23.63 |
| 2007/0233264 A1 * | 10/2007 | Nycz et al. | 623/18.11 |

* cited by examiner

*Primary Examiner* — Bruce E Snow
*Assistant Examiner* — Melissa Hoban
(74) *Attorney, Agent, or Firm* — Sorell Lenna & Schmidt LLP

(57) ABSTRACT

Methods and compositions are provided for reduction of inflammation and improved allograft/host tissue integration comprising placing at least one anti-inflammatory compound onto a site of the defect and placing a graft structure onto the site of the defect.

17 Claims, No Drawings

USE OF ANTI-INFLAMMATORY COMPOUNDS WITH ALLOGRAFT TISSUE IMPLANTATION

FIELD OF THE INVENTION

The present invention relates to methods of reducing inflammation which often accompanies allograft procedures including, bone, cartilage, tendon, and ligament grafting procedures.

BACKGROUND OF THE INVENTION

Numerous approaches are being employed to improve the bone generation and repair cycle (also referred to as the bone repair cascade). Such issues are paramount in the treatment of all bone defects related to degeneration, injury, infection, malignancy, or developmental malformation. One of the approaches is a bone graft procedure. The source of the graft may come from the subject suffering from the bone defect, or so-called autologous bone. Clearly, the use of autologous bone minimizes immunological complications but is accompanied by additional trauma of the subject. Currently, there are several different types of autologous bone graft substitutes that are either currently available or are in various stages of development.

Demineralized bone matrix (DBM) is a manufactured product that has been readily available for over ten years. See for example, Grafton Putty (Osteotech, Eaton-town, N.J.); DBX Putty (MTF [Musculoskeletal Transplant Foundation], available through Synthes, Paoli, Pa.); and AlloMatrix Injectable Putty (Wright Medical Technology, Arlington, Tenn.). DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present (Strates et al., (1988) *Am J Med Sci*, 296:266-9; Urist et al., (1997) *Connect Tissue Res*, 36:9-20; and Sammarco and Chang, (2002) *Foot Ankle Clin*, 7:19-41). DBM includes demineralized pieces of cortical bone to expose the osteoinductive proteins contained in the matrix. These activated demineralized bone particles are usually added to a substrate or carrier (e.g. glycerol or a polymer).

Allograft bone is a reasonable graft substitute for autologous bone. It is readily available from cadavers and avoids the surgical complications and subject morbidity associated with harvesting autologous bone. Allograft bone is essentially a load-bearing matrix comprised of cross-linked collagen, hydroxyapatite, and osteoinductive Bone Morphogenetic Proteins (BMP). Human allograft tissue is widely used in orthopedic surgery. Allograft tissue is strong, integrates with the recipient host bone, and can be shaped either by the surgeon to fit the specific defect or shaped commercially by a manufacturing process. Allograft bone is available in two basic forms: cancellous and cortical. Cortical bone is a highly dense structure comprised of triple helix strands of collagen fiber reinforced with hydroxyapatite. The hydroxyapatite component is responsible for the high compressive strength and stiffness of bone while the collagen fiber component contributes to its elastic nature, as well as torsional, shear, and tensile strength. Cortical bone is the main load-bearing component of long bones in the human body.

If the source of the bone graft material is not autologous, a common drawback of bone graft procedures is that the implantation of heterogeneous material into the host bone can initiate an inflammatory response. The inflammatory response is mediated by the production of catabolic cytokines by macrophages that migrate to the allograft surface attempting to remove the foreign body. The purpose of the inflammatory cascade is to promote healing of the damaged tissue, but once the tissue is healed, the inflammatory process does not necessarily end. Left unchecked, this ongoing inflammation can lead to degradation of surrounding tissues and associated chronic pain. Additionally, the inflammation results in delayed allograft incorporation with the host tissue or possibly complete rejection and resorption of the graft. Further, contemporary surgical techniques dealing with treatment of bone defects at or adjacent to the epiphyses of the bones fail to properly promote formation and integration of hylan cartilage.

Accordingly, there is a need for novel compositions and methods leading to improved clinical outcomes of bone grafting.

SUMMARY OF INVENTION

The present invention fills the foregoing need by providing devices, systems and methods for repairing a bone and soft tissue defects in a subject, wherein said bone and soft tissue defects are repairable by a bone or soft tissue graft procedure comprising placing at least one anti-inflammatory compound onto a site of the bone or soft tissue defect, and placing a bone or soft tissue graft structure onto the site of the bone or soft tissue defect. The present invention contemplates the use of allografts such as for example, osteochondral plugs comprising an anti-inflammatory compound. In several aspects of the invention, the anti-inflammatory compound is applied to the osteochondral plug at the time of processing, in its packaging, or preferably during the time of implantation.

The present invention provides that the anti-inflammatory will reduce the production of catabolic cytokines by macrophages that migrate to the allograft surface attempting to remove the foreign body. The present invention also provides reduction of catabolic cytokines, will allow the allograft osteochondral plug to become incorporated with the host tissue faster ultimately resulting in a better healed cartilage surface, and integration of the plug's hylan cartilage. The present invention provides improved integration of allograft/host tissue resulting in a more mechanically durable graft.

In several further aspects of the invention, the at least one anti-inflammatory compound can be incorporated into a carrier which is placed onto the site of the bone defect, preferably, from about 1 to about 120 minutes before the bone graft structure is placed onto the site of the bone defect. Further, different additives can be added either to the bone defect site or to the bone graft structure and the bone graft structure can also be modified. Even further, the at least one anti-inflammatory compound and, optionally, the additive may be presented in a sustained-release formulations.

Another aspect of the invention provides for the anti-inflammatory compound to be applied directly to the graft structure, on a biodegradable carrier, such as, for example, a collagen plug placed at the base of the prepared base hole or around the defect, or via injection into a synovial joint capsule. In another aspect, the invention provides a method for repairing a bone or soft tissue defect in a subject, wherein said bone or soft tissue defect is repairable by a grafting procedure comprising introducing at least one anti-inflammatory compound into a synovial joint capsule adjacent to a bone having the bone defect, and placing a graft structure onto the site of the bone defect. In different embodiments, the at least one anti-inflammatory compound can be introduced into the synovial joint capsule adjacent to a bone having the bone defect, preferably, from about 1 to about 120 minutes before the bone graft structure is placed onto the site of the bone defect. Further, different additives can be added either to the synovial joint capsule or to the graft structure, and the graft structure can also be modified. Even further, the at least one anti-inflammatory compound and, optionally, the additive, may be presented in a sustained-release formulations.

DETAILED DESCRIPTION

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.
Definitions To aid in the understanding of the invention, the following non-limiting definitions are provided:

The term "additive" shall mean any molecule, cell, intracellular structure, or any combination thereof. As a way of a non-limiting example, both a molecule, such as, for example, rhBMP-2, and a cell, such as, for example, osteoclast, are included within the meaning of the term "additive."

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "composite bone" shall mean a composition of matter comprising a polymer and demineralized bone particles.

The term "microspheres" shall mean generally spherical particles 10 µm-100 µm in size. Microspheres comprise a hollow space encapsulated by lipids, polymers, at least one surfactant, or any combination thereof, wherein the hollow space comprises therapeutic agent, such as, for example, at least one anti-inflammatory compound and/or an additive. In different embodiments, microspheres may include microbubbles and liposomes.

The term "morbidity" refers to the frequency of the appearance of complications following a surgical procedure or other treatment.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "subject" shall mean any animal belonging to phylum Chordata, including, without limitation, humans.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the subject.

The term "xenograft" refers to tissue or organs from an individual of one species transplanted into or grafted onto an organism of another species, genus, or family.

The present invention provides an advantageous strategy for reducing inflammation associated with grafting procedure. By way of example only, disclosed are compounds and methods for reducing inflammatory response associated with grafting procedure.

In one embodiment, the at least one anti-inflammatory compound is placed onto the site of the bone or soft tissue defect and a bone or soft tissue graft structure is placed onto the site of the bone or soft tissue defect. In this embodiment, the bone or soft tissue grafting structure is not modified with the at least one anti-inflammatory compound prior to the placement onto the site of the bone or soft tissue defect.

In another embodiment, the at least one anti-inflammatory compound is applied to the bone or soft tissue graft structure. Methods of application of the at least one anti-inflammatory compounds are known in the art and include, without limitation, soaking the graft tissue in a solution comprising the at least one anti-inflammatory compound, freeze drying the at least one anti-inflammatory compound onto the graft structure, injections of the at least one anti-inflammatory compound into the graft structure in situ, spraying the at least one anti-inflammatory compound on the graft structure. If the at least one anti-inflammatory compound is incorporated into a carrier as described above, the carrier may be wrapped around or layered on the graft structure.

Anti-Inflammatory Compounds:

Suitable anti-inflammatory compounds include the compounds of both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting example of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The variety of compounds encompassed by this group are well-known to those skilled in the art. For detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference.

Mixtures of these non-steroidal anti-inflammatory compounds may also be employed, as well as the pharmologically acceptable salts and esters of these compounds.

In addition, so-called "natural" anti-inflammatory compounds are useful in methods of the disclosed invention. Such compounds may suitably be obtained as an extract by suitable physical and/or chemical isolation from natural sources (e.g., plants, fungi, by-products of microorganisms). Suitable non-limiting examples of such compounds include candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, sea whip extract, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Carriers:

The at least one anti-inflammatory compound may be included into a carrier which is placed into the site of the bone defect. Suitable non-limiting examples of the carriers include a collagen sponge or a gel, such as, for example, a PEG gel. The methods of incorporating the at least one anti-inflammatory compound into the carrier are known to a person of ordinary skill in the art and depend on the nature of the at least one anti-inflammatory compound and the nature of the carrier selected by a person practicing the current invention. Ionic binding, gel encapsulation or physical trapping inside the carrier, iontophoresis and soaking the carrier in a solution of the at least one anti-inflammatory compound are suitable examples of such methods.

Additives:

In different embodiments of the invention, an additive may also be added to the carrier at the site of the bone defect or to the bone graft structure. The additive may include a growth factor, an antibiotic, a cell, an analgesic, or any combination thereof.

Suitable growth factors include, without limitation, BMP-2, rhBMP-2, BMP-4, rhBMP-4, BMP-6, rhBMP-6, BMP-7-[OP-1], rhBMP-7, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), rhGDF-5, or any combination thereof.

Suitable cell types include, without limitation, mesenchymal stem cells, periosteal cells, pluripotent stem cells, embryonic stem cells, osteoprogentior cells, osteoblasts, osteoclasts, bone marrow-derived cell lines, and any combination thereof.

Generally, anti-inflammatory non-steroid drugs are included in the definition of "analgesics" because they provide pain relief. However, in this disclosure, anti-inflammatory non-steroid drugs are included in the definition of anti-inflammatory compounds. Accordingly, the definition of the term "analgesics" for the purposes of the current disclosure does not include anti-inflammatory compounds. Thus, suitable analgesics include other types of compounds, such as, for example, opioids (such as, for example, morphine and naloxone), local anaesthetics (such as, for example, lidocaine), glutamate receptor antagonists, α-adrenoreceptor agonists, adenosine, canabinoids, cholinergic and GABA receptors agonists, and different neuropeptides. A detailed discussion of different analgesics is provided in Sawynok et al., (2003) *Pharmacological Reviews*, 55:1-20, the content of which is incorporated herein by reference.

Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, timidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

A person of ordinary skill in the art will appreciate that both the at least one anti-inflammatory compound and the additive may also be delivered on the carrier and/or in a sustained-release formulation.

Sustained-Release Formulations:

In another embodiment of the present invention, the at least one anti-inflammatory compound, and, optionally, the additive may be presented in a sustained-release formulation. Suitable sustained-release formulations include but not limited to capsules, microspheres, particles, gels, coating, matrices, wafers, pills or other pharmaceutical delivery compositions. The examples of such sustained-release formulations have been described previously, for example, in U.S. Pat. Nos. 6,953,593, 6,946,146, 6,656,508, 6,541,033, 6,451,346, the contents of which are incorporated herein by reference. Many methods of preparation of a sustained-release formulation are known in the art and are disclosed in *Remington's Pharmaceutical Sciences* (18th ed.; Mack Publishing Company, Eaton, Pa., 1990), incorporated herein by reference.

Generally, the at least one anti-inflammatory compound and/or the additive can be entrapped in semipermeable matrices of solid hydrophobic polymers. The matrices can be shaped into films or microcapsules.

Examples of such matrices include, but are not limited to, polyesters, copolymers of L-glutamic acid and gamma ethyl-L-glutamate (Sidman et al. (1983) *Biopolymers* 22:547-556), polylactides (U.S. Pat. No. 3,773,919 and EP 58,481), poly-lactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15:167-277; Langer (1982) *Chem. Tech.* 12:98-105), non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(-)-3-hydroxybutyric acid (EP 133,988), hyaluronic acid gels (see, for example, U.S. Pat. No. 4,636,524), alginic acid suspensions, polyorthoesters (POE), and the like.

Suitable microcapsules can also include hydroxymethylcellulose or gelatin-microcapsules and polymethyl methacrylate microcapsules prepared by coacervation techniques or by interfacial polymerization. See the PCT publication WO 99/24061 entitled "Method for Producing Sustained-release Formulations," wherein a protein is encapsulated in PLGA microspheres, herein incorporated by reference. In addition, microemulsions or colloidal drug delivery systems such as liposomes and albumin microspheres, may also be used. See *Remington's Pharmaceutical Sciences* (18$^{th\ ed}$.; Mack Publishing Company Co., Eaton, Pa., 1990). Other preferred sustained-release compositions employ a bioadhesive to retain the at least one anti-inflammatory compound and/or the additive at the site of administration.

The sustained-release formulation may comprise a biodegradable polymer, which may provide for non-immediate release. Non-limiting examples of biodegradable polymers suitable for the sustained-release formulations include poly (alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described, for example, in the U.S. Pat. Nos. 6,991,654 and 20050187631, each of which is incorporated herein by reference in its entirety.

A person of ordinary skill will appreciate that different combinations of the sustained-release formulations are also suitable for this invention. For example, the practitioner may formulate the at least one anti-inflammatory compound as a combination of a gel and microspheres loaded with the at least one anti-inflammatory compound, wherein the combination of gel and microspheres are placed in the bone defect.

In the practice of the invention, the administration is localized and sustained. For example, depending on the carrier, the sustained-release formulations, and the total amount of the at least one anti-inflammatory compound, the practitioner can choose a combination, which will release the at least one anti-inflammatory compound over a desired time period ranging between about one day and about six months.

In yet other embodiments, further excipients are employed. The amount of excipient that is useful in the composition of this invention is an amount that serves to uniformly distribute the at least one anti-inflammatory compound throughout the composition so that it can be uniformly dispersed when it is to be delivered to a subject in need thereof. It may serve to dilute the at least one anti-inflammatory compound to a concentration at which the at least one anti-inflammatory compound can provide the desired beneficial palliative or curative results while at the same time minimizing any adverse side effects that might occur from too high a concentration. It may also have a preservative effect. Thus, for the at least one anti-inflammatory compound that has high physiological activity, more of the excipient will be employed. On the other hand, for the at least one anti-inflammatory compound that exhibits a lower physiological activity a lesser quantity of the excipient will be employed. In general, the amount of excipient in the composition will be between about 50% weight (w) and 99.9% w. of the total composition. For the at least one anti-inflammatory compound that has a particularly high physiological activity, the amount will be between about 98.0% and about 99.9% w.

Accordingly, the methods of creating the sustained-release formulations comprising the at least one anti-inflammatory compounds and/or the additive are within the expertise of the person having ordinary skill in the art.

Bone and Soft Tissue Graft Structures:

The instant invention can be practiced with different bone or soft tissue graft structures. For example, suitable bone graft structures may include cartilage, cortical bone, cancellous bone, subchondral bone, and any combination of the various bone tissue types. In addition, bone-tendon-bone allografts used for ACL reconstruction and structures employed for long bone allograft tumor reconstruction can also be used. The present invention also contemplates, among other suitable graft candidates, the use of osteochondral plugs from autograft, allograft, and xenograft bone sources.

In medicine, the term soft tissue refers to tissues that connect, support, or surround other structures and organs of the body. Suitable soft tissue graft structures include, without limitation, muscles, ligaments, tendons (bands of fiber that connect muscles to bones), fibrous tissues, fat, blood vessels, nerves, and synovial tissues (tissues around joints). An additional soft tissue graft structure contemplated by the present invention includes for example the inner ear.

In practice, allograft is advantageous because it is readily available from cadavers, avoids additional trauma necessarily accompanying obtaining the graft structure from an autograft source and avoids the immunological complications, such as, for example, graft rejection, which accompanies a xenograft more often than the allograft.

In another embodiment of the invention, the graft structure may comprise a composite bone which includes a polymer and a demineralized bone, and, optionally, a bone powder. These compounds may be used in different ratios which can be determined by a person of ordinary skill in the art. A non-limiting example of the suitable composite bone includes 50% polylactide (PLA), 30% demineralized bone (<80 micron), and 20% bone particles (<80 micron).

A person of ordinary skill in the art will appreciate that the graft structure may be modified. For example, the ionic forces of the bone graft structure may be changed by a one-to-one substitution of the calcium ion with an element selected from the group consisting of lithium, sodium, potassium and cesium ions of hydroxyapatite. In another embodiment, the ionic forces on the surface of the graft structure may be changed by subjecting the graft structures to oxygen plasma treatment, as described in a co-pending application Ser. No. 11/339,781. These modifications will attract different cells and molecules, such as, for example, those described as additives above and those naturally present at the site of the bone or soft tissue defect.

It has been known in the art that certain molecules, such as, for example, growth factors, including, without limitation, rhBMP-2, and cells, including, without limitation, mesenchymal stem cells, periosteal cells, pluripotent stem cells, embryonic stem cells, osteoprogentior cells, osteoblasts, osteoclasts, cells from bone marrow-derived cell lines, promote the integration between the graft structure and the host tissue. Accordingly, it would be advantageous to impregnate the modified or unmodified graft structures with any combination of the molecules or the cells, which improve integration between the host tissue and the graft structure. A person of ordinary skill in the art will appreciate that the additive molecules may be incorporated into the graft structure by the same methods as can be used for incorporating the at least one anti-inflammatory compound into the graft structure, as described above. Similarly, the cells of choice may be incorporated into the graft structure by soaking the graft structure in the suspension of the cells of choice for between about 1 and about 120 minutes before applying the graft structure to the site of the defect.

Injection of at Least One Anti-inflammatory Compound into a Synovial Joint Capsule:

In another embodiment of the invention, the at least one anti-inflammatory compound and, optionally, the at least one additive may be injected into the synovial joint capsule. This embodiment is especially preferable if the bone defect is in or near an epiphysis of the host bone.

So far, integration of hylan cartilage has not been observed using contemporary surgical techniques. The injection of the at least one anti-inflammatory compound, and, optionally, the at least one additive will result in a better integration of hylan cartilage and bone tissue thus leading to a more mechanically durable graft.

A person skilled in the art will appreciate that various modifications of this embodiment are possible. Among these modifications are different sustained-release formulations of the at least one anti-inflammatory compound and, optionally, the additive.

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method for repairing a bone defect in a subject, wherein said defect is repairable by a grafting procedure comprising:

modifying a graft structure comprising an allograft bone structure, wherein the allograft bone structure is an osteochondral plug, with at least one anti-inflammatory compound that is a non-steroidal anti-inflammatory compound contained in microspheres and uniformly distributed throughout the osteochondral plug having a particle size of between 10 μm and 100 μm and a nitroimidazole antibiotic, wherein the osteochondral plug comprises hylan cartilage, demineralized bone, bone powder and a polymer and the graft structure is modified between about 1 minute and about 120 minutes before the graft structure is placed onto the site of the bone defect, and placing the graft structure onto the site of the defect.

2. The method of claim 1, wherein the graft structure is modified by a technique selected from the group consisting of freeze drying the at least one anti-inflammatory compound onto the graft structure, injections into the graft structure in situ, spraying the at least one anti-inflammatory compound on the graft structure, soaking the graft structure in a solution comprising the at least one anti-inflammatory compound, iontophoresis, and any combination thereof.

3. The method of claim 1, wherein said at least one anti-inflammatory compound is incorporated into a carrier.

4. The method of claim 3, wherein said carrier is selected from the group consisting of a collagen sponge, a synthetic polymer, a natural polymer, and any combination thereof.

5. The method of claim 3, wherein a concentration of said at least one anti-inflammatory compound is between 0.1 and 25 mg per cubic centimeter of the carrier.

6. The method of claim 1, wherein the graft structure is selected from at least one material selected from the group consisting of cortical bone, cancellous bone, subchondral bone, composite bone, structures employed for long bone allograft tumor reconstruction, and any combinations thereof.

7. The method of claim 1, wherein the graft structure includes an additive selected from the group consisting of growth factors, cells, an additional antibiotic, analgesics, and any combination thereof.

8. The method of claim 7, wherein the additive is rhBMP-2.

9. The method of claim 1, wherein at least a portion of the graft structure is modified by an ionic force change agent.

10. The method of claim 9, wherein the ionic force change agent is an oxygen plasma.

11. The method of claim 1, wherein said at least one anti-inflammatory compound is a TNF inhibitor.

12. The method of claim 1, further comprising a step of placing onto the site of the tissue defect an additive selected from the group consisting of growth factors, cells, an additional antibiotic, analgesics, and any combination thereof.

13. The method of claim 12, wherein the additive is rhBMP-2.

14. The method of claim 12, wherein the additive is incorporated into a carrier.

15. The method of claim 12, wherein the additive is in a sustained-release formulation.

16. The method of claim 1, wherein said at least one anti-inflammatory compound is placed onto the site of the bone defect from about 1 minute to about 120 minutes before the graft structure is placed onto the site of the bone defect.

17. The method of claim 1 wherein the at least one anti-inflammatory compound is in a sustained-release formulation.

* * * * *